United States Patent [19]

DiSpirito et al.

[11] Patent Number: 5,766,551
[45] Date of Patent: Jun. 16, 1998

[54] DEVICE FOR QUANTITATION OF ODORS FROM LIQUID LIVESTOCK WASTES

[75] Inventors: Alan A. DiSpirito; James A. Zahn, both of Ames, Iowa

[73] Assignee: Iowa State University Research Foundation, Inc., Ames, Iowa

[21] Appl. No.: 673,626

[22] Filed: Jun. 26, 1996

Related U.S. Application Data

[60] Provisional application No. 60/000,712 Jun. 29, 1995.
[51] Int. Cl.$^6$ ................................................. G01N 30/08
[52] U.S. Cl. ........................... 422/88; 73/19.1; 73/23.34; 73/31.02; 73/866.5; 422/93; 422/101; 422/104; 588/260
[58] Field of Search ........................... 436/177, 178, 436/181; 422/83, 88, 93, 94, 99, 101, 102, 104; 588/260; 73/19.01, 19.09, 19.1, 19.12, 23.34, 31.02, 31.03, 863.21, 863.23, 863.81, 866.5

[56] References Cited

U.S. PATENT DOCUMENTS

| | | |
|---|---|---|
| 3,198,000 | 8/1965 | Schlageter . |
| 3,800,595 | 4/1974 | Vincent .................................. 73/19.1 |
| 3,839,902 | 10/1974 | Scott et al. ............................. 73/19.01 |
| 4,863,692 | 9/1989 | Plumb ...................................... 422/58 |
| 4,919,892 | 4/1990 | Plumb ...................................... 422/58 |

*Primary Examiner*—Jan Ludlow
*Attorney, Agent, or Firm*—Zarley, McKee, Thomte, Voorhees, & Sease

[57] ABSTRACT

The gas sample device structure has a housing with a continuous normally vertical sidewall, closed top and an open bottom. Buoyant elements are secured to the housing to maintain its vertical position in a body of liquid livestock waste. A normally closed compartment is located on the top of the housing. A partition is located within the closed compartment to divide it into first and second subcompartments. An opening is provided in the closed top of the housing to allow gases from liquid manure in the housing to move into the first subcompartment. One or more hollow gas detection tubes are mounted in the second subcompartment and have a first open end in communication with the interior of the first subcompartment to receive gases from within the first compartment. The method of the invention involves placing the housing in a liquid manure lagoon so its buoyancy is maintained by the buoyancy elements, but the lower portion thereof is submerged in the liquid manure. The gases rise from the liquid into the upper end of the housing and through a suitable opening into a closed compartment on top of the housing where the gases are caused to move through gas detection tubes for a period of time.

7 Claims, 3 Drawing Sheets

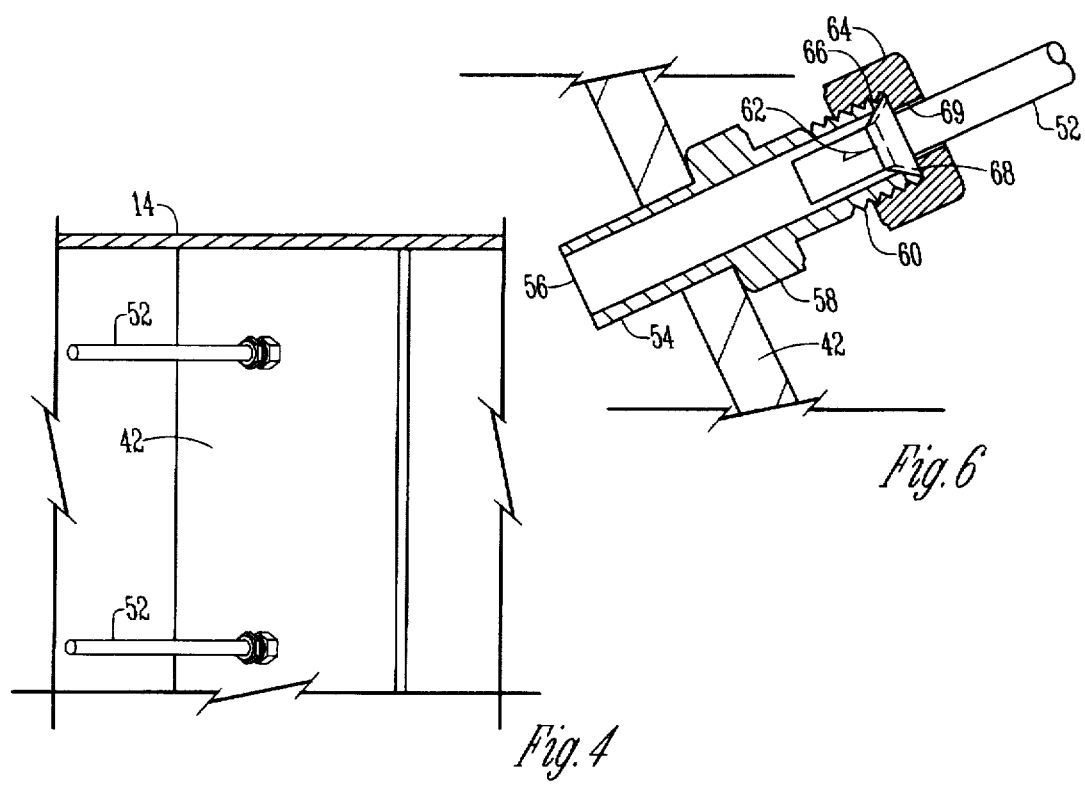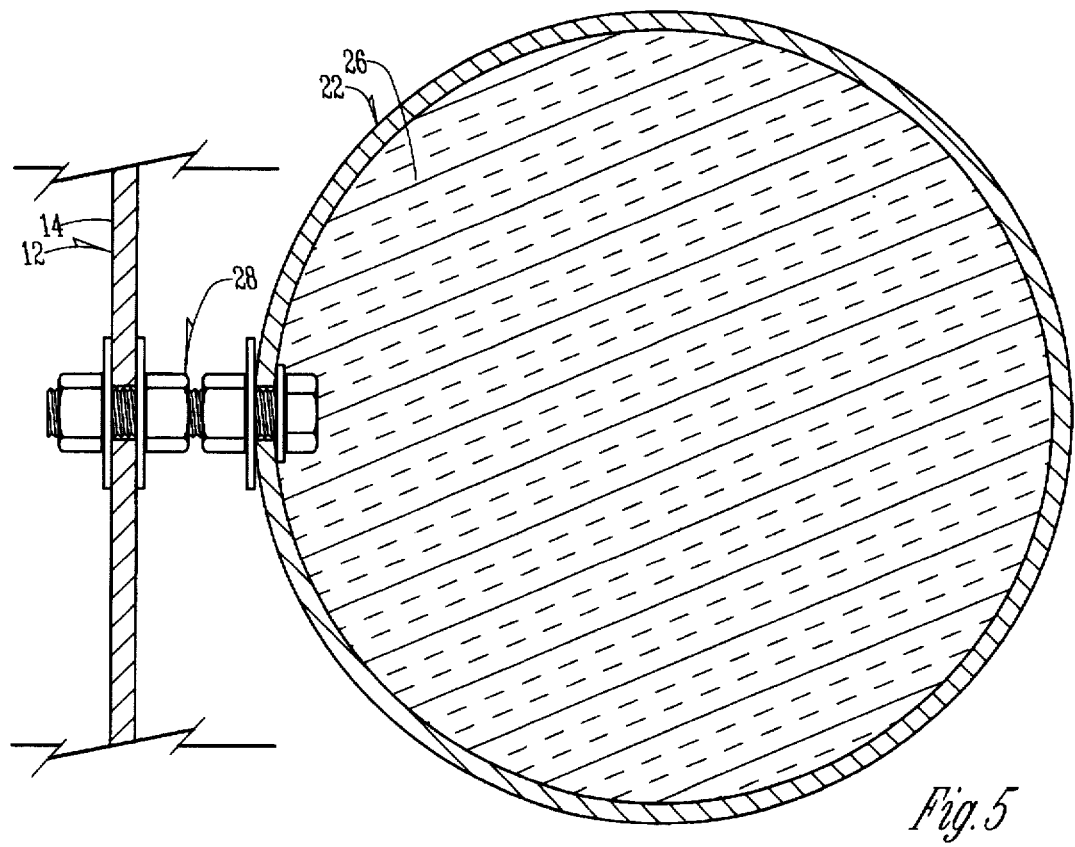

1

DEVICE FOR QUANTITATION OF ODORS FROM LIQUID LIVESTOCK WASTES

This application is based upon the applicants' Provisional application Ser. No. 60/000,712 filed Jun. 29, 1995.

BACKGROUND OF THE INVENTION

Processing of livestock wastes usually involves the collection and storage in deep above ground or pit holding sites. Unless an aeration system is used, the storage system becomes anaerobic and odors from the storage system and/or confinement building can become a problem. Over 2000 different volatile compounds have been identified in air samples from livestock waste storage/treatment systems. Although several of these compounds are individually regulated by the federal law (i.e. Clean Air Act), taken as a group livestock odors are not regulated by federal laws. Air quality from livestock production facilities is controlled in many areas by state and local regulations such as providing minimum distance standards between anaerobic lagoons and residences or public lands.

To protect individuals living in the vicinity of livestock production facilities, as well as the owners of such facilities, odor emission guidelines at the state or local government level must be developed. However, before these guidelines can be enacted, standard methods of odor measurements must be developed. The lack of a standard method of odor measurement has also made evaluation of odor control methods/technologies impossible.

It is therefore a principal object of this invention to provide a method and means for sampling odors from livestock waste so that they can be appropriately analyzed to determine and identify volatile inorganic and organic compounds within gases emitted from liquid animal wastes.

A further object of this invention is to provide a method and means for collecting samples of gas emitted by liquid livestock waste which is easy and efficient to use, and inexpensive to build and to operate.

These and other objects will be apparent to those skilled in the art.

SUMMARY OF THE INVENTION

The device of this invention comprises a housing having a continuous normally vertical sidewall, closed top and a bottom sufficiently open to receive liquid livestock waste. Buoyant elements are secured to the housing and are positioned to maintain its buoyancy and to maintain its sidewall in a substantially vertical position in a body of liquid livestock waste. A normally closed compartment is located on the top of the housing. A partition is located within the closed compartment to divide it into first and second subcompartments. An opening is provided in the closed top of the housing to allow gases from liquid manure in the housing to move into the first subcompartment. One or more hollow gas detection tubes are mounted in the second subcompartment and have a first open end in communication with the interior of the first subcompartment to receive gases from within the first compartment. The gas detection tube is filled with a chemical material or materials to intercept indices of volatile inorganic and organic compounds within the gas passing therethrough. The tubes are removably mounted and are then analyzed to determine the precise identity of such compounds.

The method of the invention involves placing the housing in a liquid manure lagoon or the like so its buoyancy is maintained by the buoyancy elements, but the lower portion thereof is submerged in the liquid manure. The gases rise from the liquid into the upper end of the housing and through a suitable opening into a closed compartment on top of the housing where the gases are caused to move through gas detection tubes for a period of time. The tubes are subsequently removed and analyzed as to the type of organic and inorganic compounds that are contained in the gases passing through the tubes.

BRIEF DESCRIPTION OF THE DRAWINGS

FIG. 4 is a partial plan view taken on line 4—4 of FIG. 3;

FIG. 5 is an enlarged scale sectional view taken on line 5—5 of FIG. 5; and

FIG. 6 is a large scale sectional view of the structure within line 6—6 of FIG. 3.

DESCRIPTION OF THE PREFERRED EMBODIMENT

Figure 1:
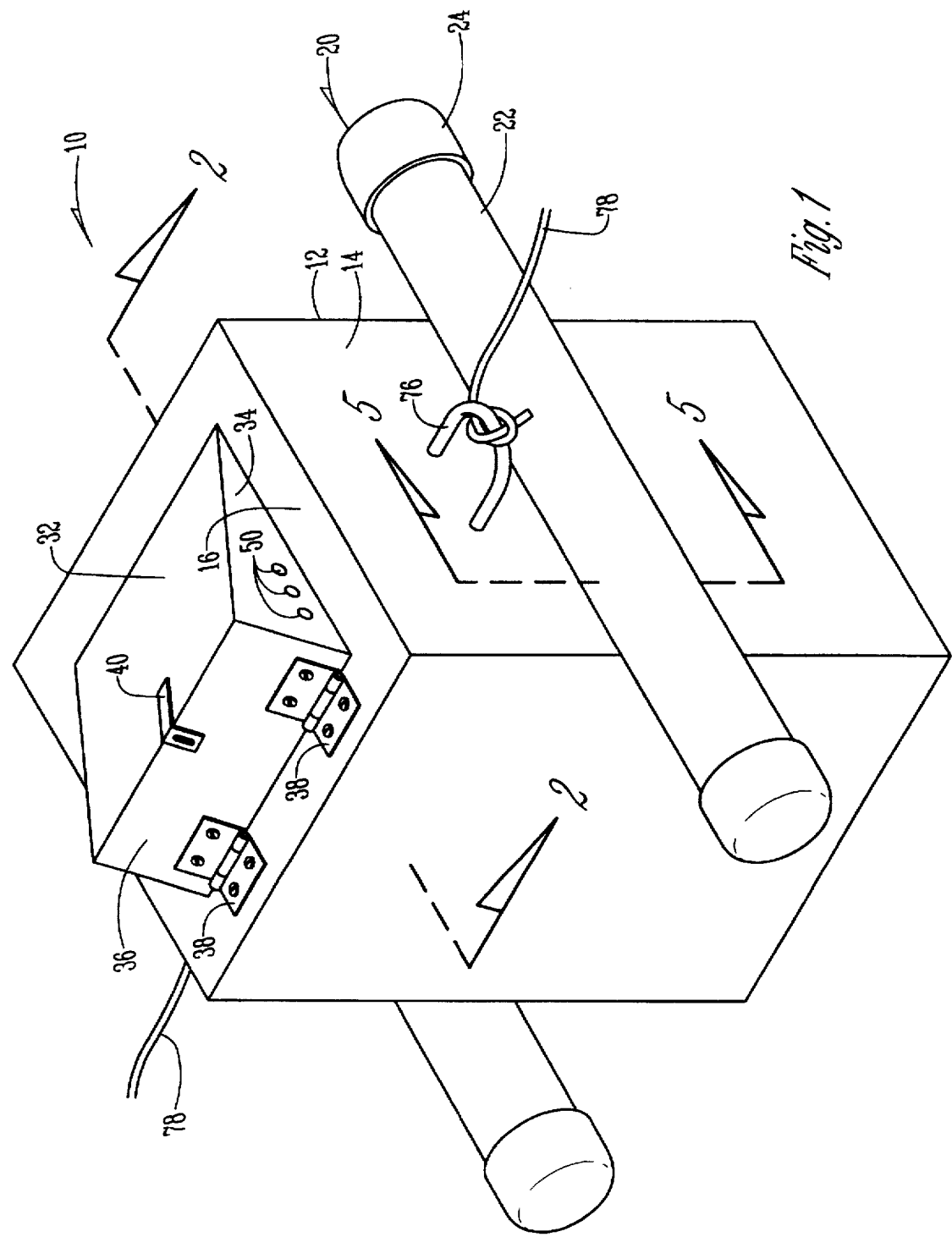
FIG. 1 is a perspective view of the apparatus of this invention.

The gas sampling device 10 of this invention comprises a housing 12, a continuous sidewall 14 preferably square in construction, a closed top 16 and an open bottom 18. (See FIGS. 1 and 2).

Elongated buoyancy elements 20 are comprised of PVC pipes 22 approximately 4" in diameter. The pipes 22 are sealed by end caps 24 and have a buoyant material such as blue foam or the like 26 (FIG. 5) contained therein so that the buoyancy is maintained even though the seal of the buoyancy elements 26 might be disturbed. The buoyancy elements 20 are secured to the sidewall 14 of housing 12 by nut and bolt assemblies 28 (FIG. 5). The buoyancy elements 20 are located at a horizontal plane passing through the center of housing 12. This insures that when the housing is placed in a liquid lagoon, the lower portion thereof will be submerged in the lagoon with the upper portion containing only air and gases from the lagoon.

A closed compartment 30 is secured in any convenient fashion to the closed top 16 of housing 12. The closed compartment has a sloping top 32 and triangular shaped sides 34. A front or lid 36 is secured to the closed top 16 by hinges 38. A latch 40 secures the upper edge of the front 36 to the upper edge of top 32.

Figure 2:
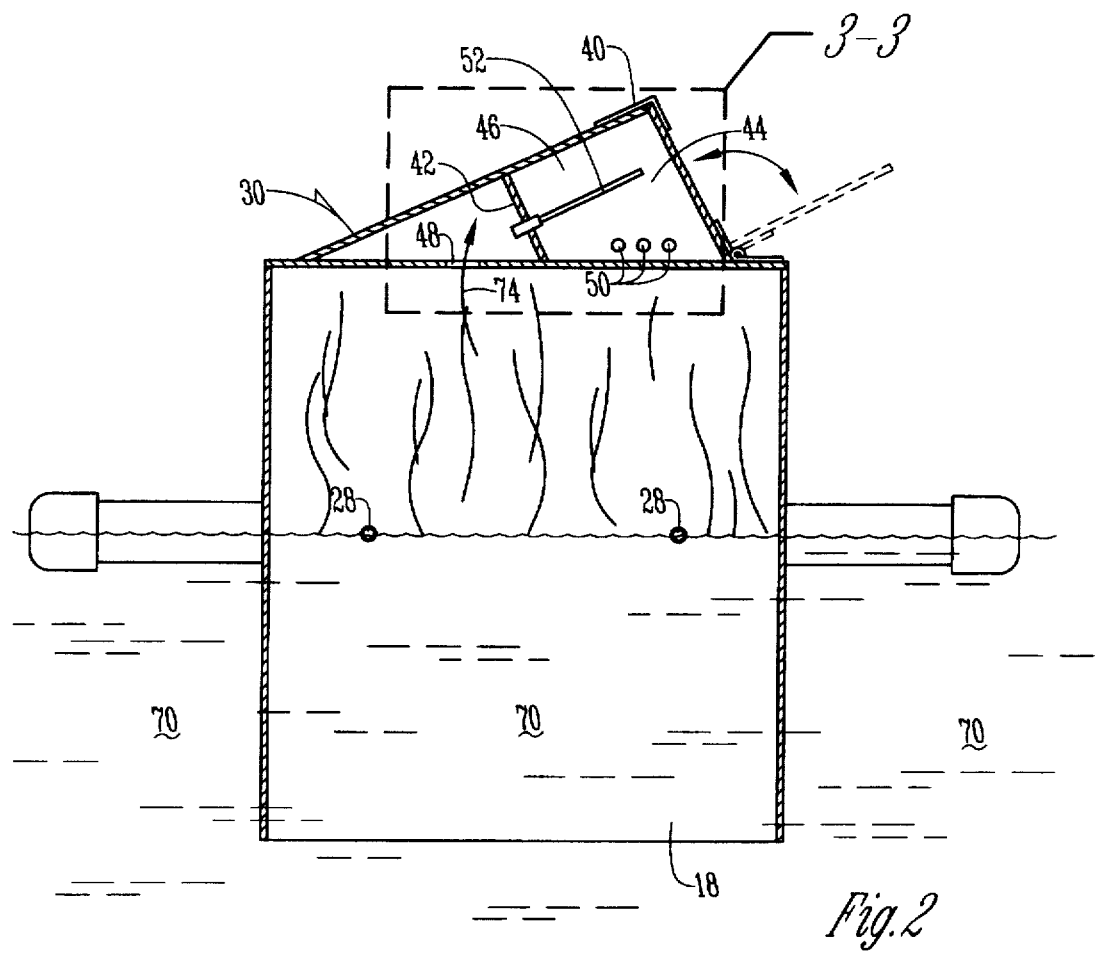
FIG. 2 is a smaller scale cross-sectional view with the device of FIG. 1 located in a liquid manure lagoon, as taken on line 2—2 of FIG. 1.
Figure 3:
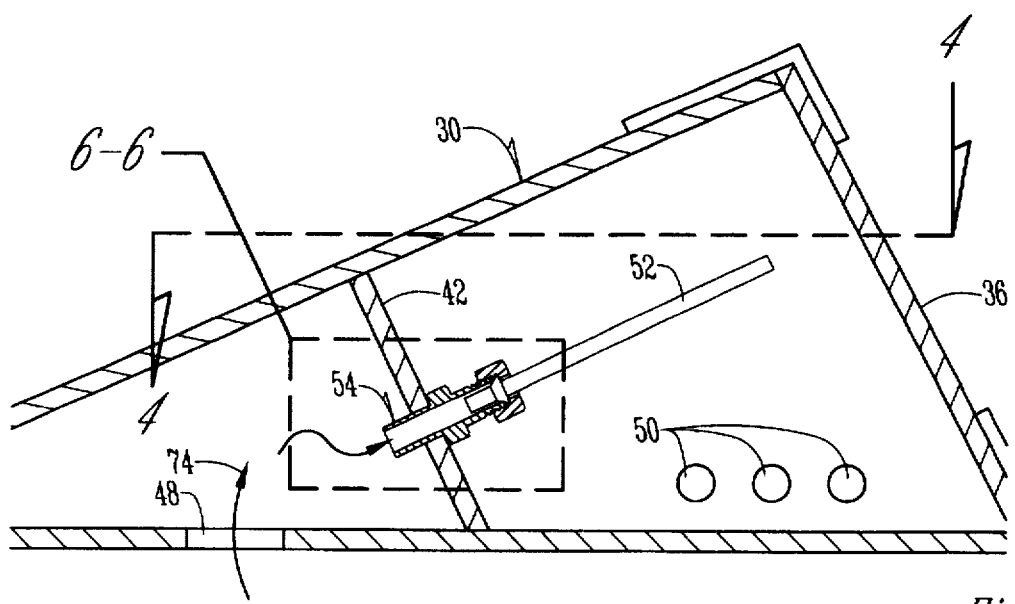
FIG. 3 is a partial large scale sectional view showing the structure within lines 3—3 of FIG. 2.

A sloping partition 42 is mounted within the closed compartment 30 as best shown in FIGS. 2 and 3. Partition 42 divides the closed compartment 30 into a first subcompartment 44 and a second subcompartment 46. A gas opening 48 is located in the closed top 16 to connect the upper portion of housing 12 with the first subcompartment 44. Vent openings 50 are located in the sidewalls 34 adjacent second subcompartment 44 to induce the flow of gases from the upper portion of housing 12 and thence through the subcompartments 44 and 46 as will be discussed hereafter.

A plurality of conventional gas detection tubes 52 are mounted on the sloping partition 42 by means of fittings 54. The fittings 54 (FIG. 6) include a tube 56 which extends through the partition and which terminates in shoulder 58 and threaded studs 60 within the second subcompartment 46. A conventional ferrule 62 having a center opening (not shown) is positioned within the outer end of threaded stud 60. One end of each of the gas detection tubes 50 is inserted through ferrule 62. A conventional nut 64 having a threaded recess 66 and a bottom 68 has a center bore 69 to receive one end of tube 52. By tightening the nut 64 on the threaded stud 60, and against ferrule 62, the tube 52 is detachably and rigidly secured within the fitting 54.

The liquid animal waste or lagoon liquid 70 is best shown in FIG. 2 and has a upper level 72. The arrow 74 in FIGS. 2 and 3 show the path of gas moving from the upper portion of housing 12 into the subcompartment 44.

Loop 76 can be secured to the outer side of sidewall 14 to have one end of tether lines 78 secured thereto. The tether lines are secured to anchors or the like at the edge of the typical lagoon to stabilize the position of the gas sampling device 10.

The housing 12 and the structure of compartment 30 is typically made of plexiglas.

In operation, the gas detection tubes 52 contain one or more chemicals that have the capability of detecting indices of volatile inorganic and organic compounds. Typical chemicals used in tubes 52 are a silica base material such as Tenax TA (100 mg) (produced by Alltech, Deerfield, Ill.), and activated charcoal, i.e., -carbopack C (300 mg) (as produced by Supelco, Bellefonte, Pa.). After gases have been conducted through these tubes and this material for a period of time as discussed hereafter, the volatile organics are eluted from these resins within a Thermal Tube Desorber Model 890 (made by Dynatherm Analytical Instruments) and are thereafter analyzed by gas chromatography. The use of these resins and analysis thereof are conventional in the art.

The closed compartment 30 assumes its pyramid shape to reduce the height of the overall device and to prevent it from being top heavy.

Device 10 is placed in the lagoon as described above and is left for a period of several hours to several days. A plurality of the tubes 52 are utilized. When it is determined that the content thereof should be tested, the tether lines 78 are released and the device is pulled to a location where it is accessible to the operator. The front 36 is thereupon opened by loosening latch 40 and the tubes 52 are removed from the device by merely loosening the nuts 64. The tubes 52 are then analyzed by conventional procedures to determine the identity of the volatile inorganic and organic compounds that have been collected within the tube through the movement of gases from the liquid material 70 through the opening 48, into the first subcompartment 44 through the tubes 52, and thence through the second subcompartment 46 and out of the vent holes 50.

It is seen that this invention will facilitate the collection of gases from liquid waste materials. Accordingly, it is seen that this device and this method will accomplish all of the stated objectives.

What is claimed is:

1. A device for quantitation of livestock odors from liquid livestock wastes, comprising, a housing having a continuous normally vertical sidewall, a closed top, and a bottom sufficiently open to receive liquid livestock waste, buoyant elements on said housing and being positioned to maintain its buoyancy and its sidewall in a substantially vertical position in a body of liquid livestock waste, a normally closed compartment on the closed top of said housing, a partition in said closed compartment dividing said closed compartment into at least two laterally adjacent first and second subcompartments, an opening in the closed top of said housing to allow gases from liquid manure in said housing to move into said first subcompartment, and at least one elongated hollow gas detection tube mounted in said second subcompartment and having a first open end in communication with the interior of said first subcompartment to receive liquid manure gases from within said first compartment, said gas detection tube having a second open end in said second subcompartment, said gas detection tube containing one or more gas interception materials to intercept volatile inorganic and organic compounds as gas passes from said housing into said first subcompartment and thence into said second subcompartment through said gas detection tube.

2. A device for quantitation of livestock odors from liquid livestock wastes, comprising, a housing having a continuous normally vertical sidewall, a closed top, and a bottom sufficiently open to receive liquid livestock waste, said housing being closed to direct access with air outside the housing, buoyant elements on said housing and being positioned to maintain its buoyancy and its sidewall in a substantially vertical position in a body of liquid livestock waste, a normally closed compartment on the closed top of said housing, a partition in said closed compartment dividing said closed compartment into at least two laterally adjacent first and second subcompartments, an opening in the closed top of said housing to allow gases from liquid manure in said housing to move into said first subcompartment, and at least one elongated hollow gas detection tube mounted in said second subcompartment and having a first open end in communication with the interior of said first subcompartment to receive liquid manure gases from within the space of said first compartment above the level of said livestock waste therein.

3. The device of claim 2 where said second subcompartment has a closable access opening for recovery of said gas detection tube.

4. The device of claim 2 wherein a plurality of gas detection tubes are mounted in said second subcompartment.

5. The device of claim 2 wherein vent means are located in said second subcompartment to enhance gas movement from said housing through said first and second subcompartments and said gas tubes.

6. The device of claim 2 wherein said buoyant elements are comprised of several rigid hollow members filled with buoyant material.

7. The device of claim 2 wherein said housing has one or more tether lines secured thereto for stabilizing the location of said housing in a liquid manure lagoon.

* * * * *